United States Patent
Sonda

(10) Patent No.: US 7,420,671 B2
(45) Date of Patent: Sep. 2, 2008

(54) DEFECT INSPECTION METHOD AND APPARATUS FOR TRANSPARENT PLATE-LIKE MEMBERS

(75) Inventor: Yoshiyuki Sonda, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 11/752,577

(22) Filed: May 23, 2007

(65) Prior Publication Data

US 2007/0216897 A1   Sep. 20, 2007

Related U.S. Application Data

(63) Continuation of application No. PCT/JP2005/019408, filed on Oct. 21, 2005.

(30) Foreign Application Priority Data

Nov. 24, 2004   (JP) .............................. 2004-339215

(51) Int. Cl.
*G01N 21/00* (2006.01)

(52) U.S. Cl. ................................ 356/239.1; 356/239.5

(58) Field of Classification Search ... 356/237.1–237.6, 356/239.1–239.8; 382/145–154
See application file for complete search history.

(56) References Cited

U.S. PATENT DOCUMENTS 7,199,386 B2 *   4/2007   Capaldo et al. .......... 250/559.4
2005/0062961 A1 *   3/2005   Uto et al. ................. 356/237.2

FOREIGN PATENT DOCUMENTS

| JP | 58-154229 A | 9/1983 |
| JP | 8-201313 | 8/1996 |
| JP | 9-258197 A | 10/1997 |
| JP | 10-339705 | 12/1998 |
| JP | 11-264803 | 9/1999 |
| JP | 2004-233338 A | 8/2004 |

* cited by examiner

*Primary Examiner*—Gregory J. Toatley, Jr.
*Assistant Examiner*—Tri T Ton
(74) *Attorney, Agent, or Firm*—Oblon, Spivak, McClelland, Maier & Neustadt, P.C.

(57) ABSTRACT

A defect inspection method and apparatus for a transparent plate material for detecting a bubble, a scratch, a foreign matter, and another defect existing on or in the transparent plate material including regarding a defect candidate as a defect, when the defect candidate is located in both first and second images, and regarding the defect candidate as a pseudo defect, when the defect candidate is located in only one of the first and second images.

2 Claims, 14 Drawing Sheets

AA: TYPES OF DEFECTS etc.
BB: DARK SIGNAL OF CAMERA LOCATED AT MAIN SURFACE SIDE
CC: DARK SIGNAL OF CAMERA LOCATED AT REAR SURFACE SIDE

DEFECT INSPECTION METHOD AND APPARATUS FOR TRANSPARENT PLATE-LIKE MEMBERS

TECHNICAL FIELD

The present invention relates to a defect inspection method and a defect inspecting apparatus for a transparent plate material, and more particularly, to a defect inspection method and apparatus for glass substrates used for various types of display units (such as liquid crystal display (LCD) units, plasma display panel (PDP) units, electroluminescence (EL) units, field emission display (FED) units, or LCD projection TV sets), for a glass base plate for automobiles and other vehicles, and for sheet glass for buildings.

BACKGROUND ART

In the defect inspection for transparent plate materials, it is necessary to distinguish defects, such as bubbles, foreign matters, or scratches, from pseudo defects that do not affect the quality of the transparent plate materials, such as dust and grime. Depending on the positions of defects (whether defects are located on a main surface, in the inside, or on a rear surface) in the transparent plate materials and the depths of defects when they are located in the inside, the required quality level is different in some cases. Therefore, it has been demanded not only to detect defects but also to identify the positions of the defects in the thickness direction of the transparent plate materials.

In addition to these requirements for inspection performance, requirements for industrial applications are also imposed on defect inspection methods. In such requirements, the inspection performance should not be reduced depending on the sizes of transparent plate materials, the methods should be able to be applied to transparent plate materials having various thicknesses, and the methods should be able to be applied to continuous forming processes (online) for transparent plate materials, which are typically represented by a float process for flat glass.

To distinguish between defects and pseudo defects, there is a method, which uses a transmission dark-field optical system having a rod-shaped light source and a light-blocking mask combined together therein as disclosed in JP-A-8-201313. This method uses a difference in light-scattering directivity between defects and pseudo defects to distinguish between the defects and the pseudo defects. However, since light-scattering directivity differs depending on the types of defects, and since pseudo defects also exhibit various light-scattering directivity, it is difficult to distinguish between defects and pseudo defects just by light-scattering directivity. In addition, since the method disclosed in JP-A-8-201313 uses a transmission optical system, it is difficult to identify the positions of defects in the thickness direction of the transparent plate materials.

To distinguish between defects and pseudo defects, there is another method (hereinafter called an edge light method), in which light is emitted toward the inside of a transparent plate material from its end face to detect scattered light caused by a defect as disclosed in JP-A-10-339705 and JP-A-11-264803. The light incident on the end face and coming into the inside of the transparent plate material advances through the inside of the plate material, repeating total reflection. The light is scattered at a portion where a defect exists, and exits from a main surface or a rear surface of the transparent plate material. The light advancing through the inside of the transparent plate material is not scattered by a pseudo defect attached to the main surface or the rear surface of the transparent plate material. Therefore, when cameras are disposed at a main surface side and a rear surface side of the transparent plate material, only defects can be detected. In addition, by comparing detection signals sent from the cameras disposed at the main surface side and the rear surface side of the transparent plate material, the position of a defect in the thickness direction of the transparent plate material can be determined to some extent.

Patent Document 1: JP-A-8-201313
Patent Document 2: JP-A-10-339705
Patent Document 3: JP-A-11-264803

DISCLOSURE OF THE INVENTION

PROBLEMS TO BE SOLVED BY THE INVENTION

The conventional edge light method has some problems. Since light incident on a transparent plate material from an end face is absorbed by the transparent plate material itself, the amounts of light supplied to defects differ between a central part (central part in the plane) and an end part of the transparent plate material. When the transparent plate material is small, the difference in the amounts of light does not matter much. As the transparent plate material becomes larger, the difference in the amounts of light supplied becomes significant, causing an in-plane distribution in the inspection performance. As the transparent plate material increases in thickness, this situation is worsened. Therefore, the edge light method has a narrower applicable thickness range than the other methods.

Recently, especially LCD panels have been becoming much larger, from the fifth generation (1,100 mm by 1,250 mm) used conventionally to the sixth generation (1,500 mm by 1,850 mm) or to the seventh generation (1,870 mm by 2,200 mm) of the panels. Consequently, there is a strong demand for a new technology for implementing automatic substrate inspection.

In view of the circumstances described above, it is an object of the present invention to solve a problem in the conventional technology, in which inspection performance is reduced as transparent plate materials become larger. It is another object of the present invention to identify the position of a defect in the thickness direction of a transparent plate material more correctly than in the conventional technology.

MEANS FOR SOLVING THE PROBLEMS

To achieve the above-described objects, the present invention provides a defect inspection method for a transparent plate material for detecting a bubble, a scratch, a foreign matter, and another defect existing on or in the transparent plate material. The defect inspection method comprises the steps of capturing an image (hereinafter called a first image) of a main surface of the transparent plate material by using a first reflective bright-field optical system disposed at a main surface side of the transparent plate material, the first optical system including a linear light source and a camera; capturing an image (hereinafter called a second image) of a rear surface of the transparent plate material by using a second reflective bright-field optical system disposed at a rear surface side of the transparent plate material, the second optical system including a linear light source and a camera; searching for a defect candidate in each of the first and second images; and checking, based on a result of the search, whether defect candidates are located at positions corresponding to each other in the first and second images; when defect candidates are found from both the first and second images, regarding the defect candidates as a defect; and when a defect candidate is found from only one of the first and second images, regarding the defect candidate as a pseudo defect.

The present invention also provides a defect inspection method for a transparent plate material for detecting a bubble, a scratch, a foreign matter, and another defect existing on or in the transparent plate material. The defect inspection method comprises the steps of capturing an image (hereinafter called a first image) of a main surface of the transparent plate material by using a first reflective bright-field optical system disposed at a main surface side of the transparent plate material, the first optical system including a linear light source and a camera; capturing an image (hereinafter called a second image) of a rear surface of the transparent plate material by using a second reflective bright-field optical system disposed at a rear surface side of the transparent plate material, the second optical system including a linear light source and a camera; searching for a defect candidate in each of the first and second images; determining, based on the contrast of an image of a defect candidate obtained by the search, whether a real image or a virtual image was formed; and determining, based on an appearance pattern of the real image or the virtual image, whether the defect candidate is located on the main surface, inside, or on the rear surface of the transparent plate material.

The present invention also provides a defect inspection method for a transparent plate material for detecting a bubble, a scratch, a foreign matter, and another defect existing on or in the transparent plate material. The defect inspection method comprises the steps of capturing an image (hereinafter called a first image) of a main surface of the transparent plate material by using a first reflective bright-field optical system disposed at a main surface side of the transparent plate material, the first optical system including a linear light source and a camera; capturing an image (hereinafter called a second image) of a rear surface of the transparent plate material by using a second reflective bright-field optical system disposed at a rear surface side of the transparent plate material, the second optical system including a linear light source and a camera; searching for a defect candidate in each of the first and second images; obtaining the distance between two images of an identical defect candidate, appearing in an identical camera; and determining, based on the distance between the two images, whether the defect candidate is located on the main surface, inside, or on the rear surface of the transparent plate material.

Preferably, the above-described defect inspection method for a transparent plate material further comprises the step of treating the thickness of the transparent plate material as known information and obtaining the depth of the defect in the thickness direction of the transparent plate material, based on the distance between two images of the identical defect, appearing in the identical camera.

The present invention also provides a defect inspection apparatus for a transparent plate material for detecting a bubble, a scratch, a foreign matter, and another defect existing on or in the transparent plate material. The defect inspection apparatus comprises a first reflective bright-field optical system disposed at a main surface side of the transparent plate material, for capturing an image (hereinafter called a first image) of a main surface of the transparent plate material, the first optical system including a linear light source and a camera; a second reflective bright-field optical system disposed at a rear surface side of the transparent plate material, for capturing an image (hereinafter called a second image) of a rear surface of the transparent plate material, the second optical system including a linear light source and a camera; and a computer for searching for a defect candidate in each of the first and second images; for checking, based on a result of the search, whether defect candidates are located at positions corresponding to each other in the first and second images; for, when defect candidates are found from both the first and second images, regarding the defect candidates as a defect; and for, when a defect candidate is found from only one of the first and second images, regarding the defect candidate as a pseudo defect.

The present invention also provides a defect inspection apparatus for a transparent plate material for detecting a bubble, a scratch, a foreign matter, and another defect existing on or in the transparent plate material. The defect inspection apparatus comprises a first reflective bright-field optical system disposed at a main surface side of the transparent plate material, for capturing an image (hereinafter called a first image) of a main surface of the transparent plate material, the first optical system including a linear light source and a camera; a second reflective bright-field optical system disposed at a rear surface side of the transparent plate material, for capturing an image (hereinafter called a second image) of a rear surface of the transparent plate material, the second optical system including a linear light source and a camera; and a computer for searching for a defect candidate in each of the first and second images; for determining, based on the contrast of an image of a defect candidate obtained by the search, whether a real image or a virtual image was formed; and for determining, based on an appearance pattern of the real image or the virtual image, whether the defect candidate is located on the main surface, inside, or on the rear surface of the transparent plate material.

The present invention also provides a defect inspection apparatus for a transparent plate material for detecting a bubble, a scratch, a foreign matter, and another defect existing on or in the transparent plate material. The defect inspection apparatus comprises a first reflective bright-field optical system disposed at a main surface side of the transparent plate material, for capturing an image (hereinafter called a first image) of a main surface of the transparent plate material, the first optical system including a linear light source and a camera; a second reflective bright-field optical system disposed at a rear surface side of the transparent plate material, for capturing an image (hereinafter called a second image) of a rear surface of the transparent plate material, the second optical system including a linear light source and a camera; and a computer for searching for a defect candidate in each of the first and second images; for obtaining the distance between two images of an identical defect candidate, appearing in an identical camera; and for determining, based on the distance between the two images, whether the defect candidate is located on the main surface, inside, or on the rear surface of the transparent plate material.

Preferably, the above-described computer further comprises a function of treating the thickness of the transparent plate material as known information and for obtaining the depth of the defect in the thickness direction of the transparent plate material, based on the distance between two images of the identical defect, appearing in the identical camera.

EFFECTS OF THE INVENTION

As described above, according to the present invention, by using images of defect candidates appearing on or in the main surface side and the rear surface side of a transparent plate material, defects (such as bubbles, scratches, and foreign matters) and pseudo defects (such as dust and grime) can be distinguished to realize an online defect inspection. In addition, the present invention has the advantages that the position of a defect can be correctly identified in the thickness direction of the transparent plate material, that inspection performance is not reduced depending on the size of the transparent plate material, and that transparent plate materials with a wider range of thicknesses can be inspected compared with the edge light method. Furthermore, since a transparent plate material is not required to have a smooth end face in the present invention, the present invention can be also applied to sheet-glass continuous forming processes, such as the float process.

DESCRIPTION OF SYMBOLS

Figure 1:
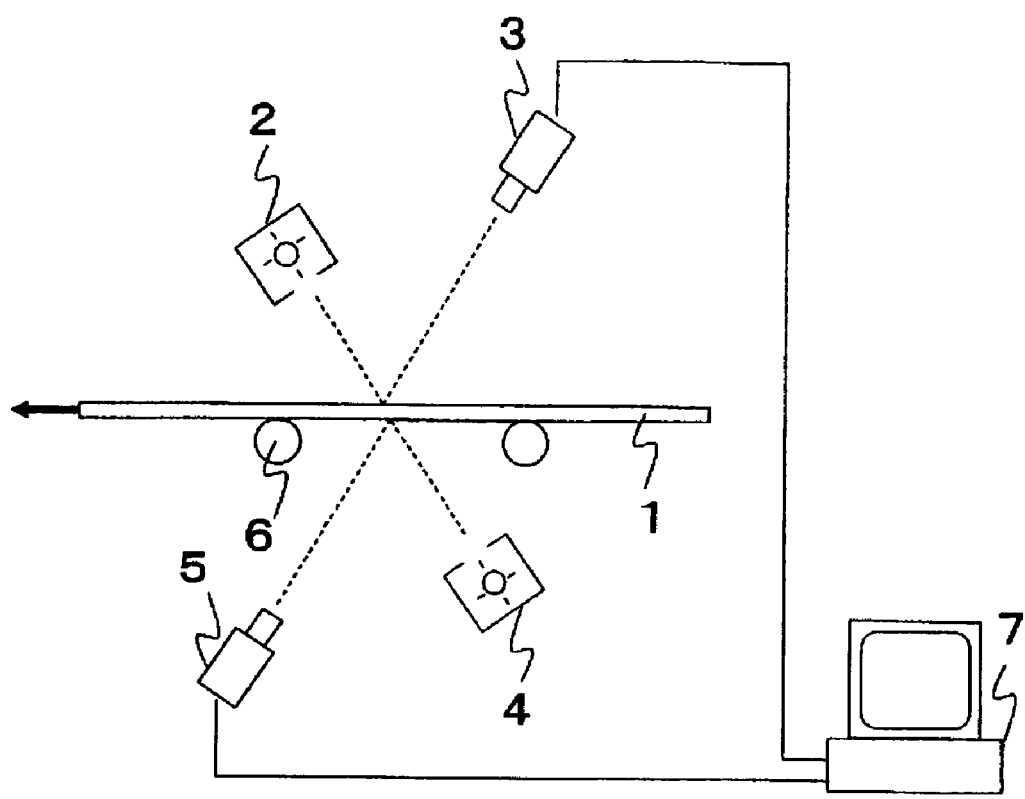
FIG. 1 is a view showing the basic structure of the present invention.

1: Transparent plate material
2, 4: Linear light sources
3, 5: Line sensor cameras
6: Conveying rollers
7: Computer
8, 9: Optical paths (upper optical system)
10, 11: Optical paths (lower optical system)
12: Defect located on a main surface of a transparent plate material
13: Defect located inside the transparent plate material
14: Defect located on a rear surface of the transparent plate material
15: Pseudo defect located on the main surface of the transparent plate material
16: Pseudo defect located on the rear surface of the transparent plate material
17: Inside defect located close to the rear surface of the transparent plate material
18: Distance between a position where the inside defect first crosses an optical path and a position where the inside defect crosses an optical path for the second time

BEST MODE FOR CARRYING OUT THE INVENTION

An embodiment of the present invention will be described next.

FIG. 1 is a view showing the basic structure of the present invention. As shown in FIG. 1, a linear light source 2 and a line sensor camera 3 are disposed above a transparent plate material 1 placed on conveying rollers 6, and a linear light source 4 and a line sensor camera 5 are disposed below the transparent plate material 1. While the transparent plate material 1 is conveyed at a constant speed by the conveying rollers 6 in the direction indicated by the arrow, the line sensor camera 3 and the line sensor camera 5 consecutively capture images of the transparent plate material. A computer 7 processes, at the same time, images obtained by both line sensor cameras and performs a defect inspection.

A step of capturing an image of a main surface of the transparent plate material 1 and a step of capturing an image of a rear surface of the transparent plate material 1 will be described first. The linear light source 2 and the light-receiving element of the line sensor camera 3 are both arranged side by side in a direction perpendicular to the sheet of the figure (the width direction of the transparent plate material 1). As a specific structure of the linear light source 2, a fluorescent light disposed in a light source box having a slit; a light guide having a linear light emitting portion, to which light from a halogen lamp or a metal halide lamp is supplied through an optical fiber; or other various light sources can be used.

The linear light source 2 is disposed at a position in the specular direction of the line sensor camera 3 with respect to the transparent plate material 1. In the same way, the linear light source 4 is disposed at a position in the specular direction of the line sensor camera 5 with respect to the transparent plate material 1. With this arrangement, a reflected image of the linear light source 2 is projected on the line sensor camera 3; a reflected image of the linear light source 4 is projected on the line sensor camera 5; and bright fields are formed respectively. Although there is no limitation to the angle formed between the normal line of the transparent plate material 1 and each of the optical axes of the line sensor cameras 3 and 5, it is preferred that the angle range from 20 to 70 degrees.

Figure 2:
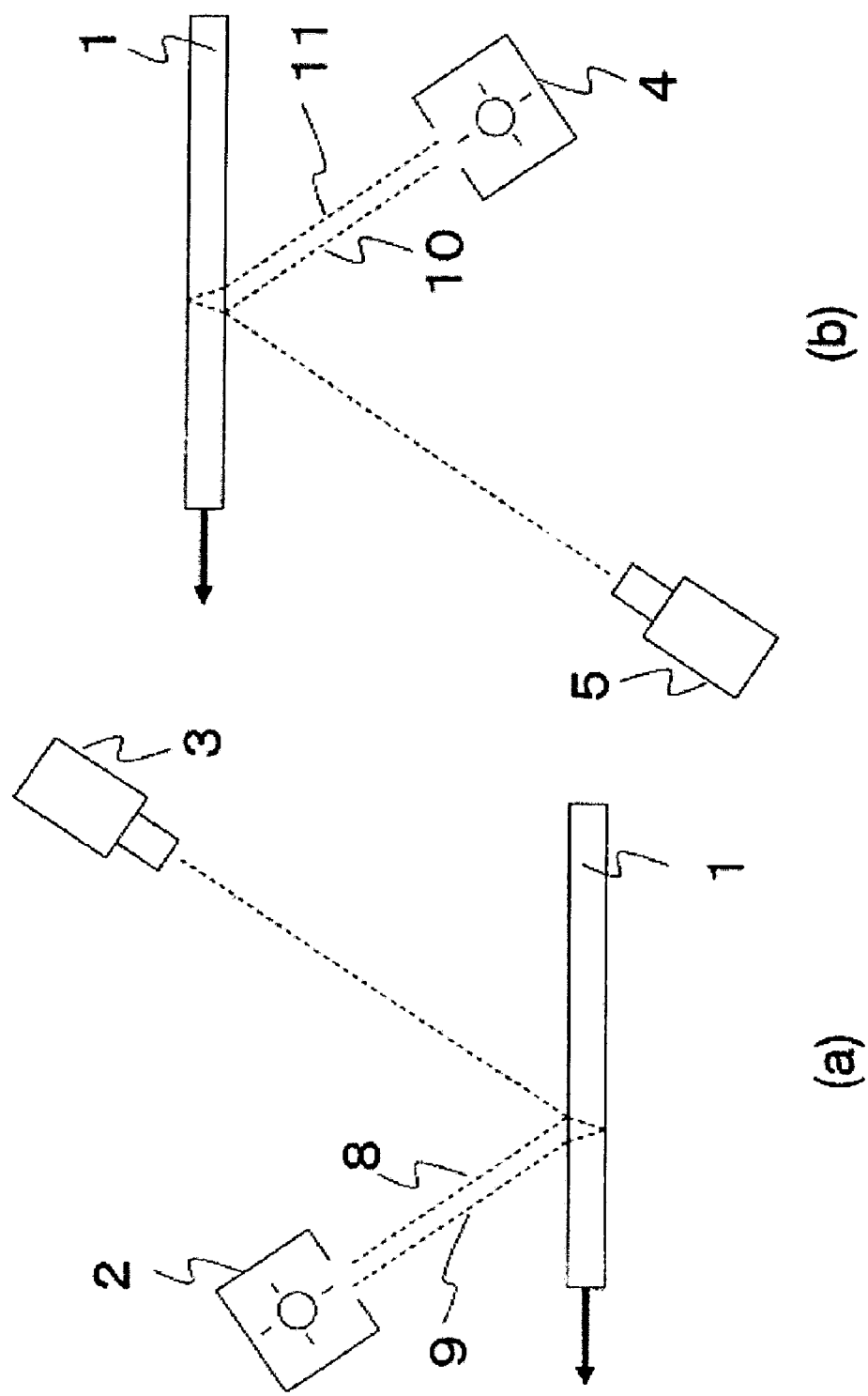
FIG. 2 includes views showing states in which upper and lower line sensor cameras have bright fields.
Figure 3:
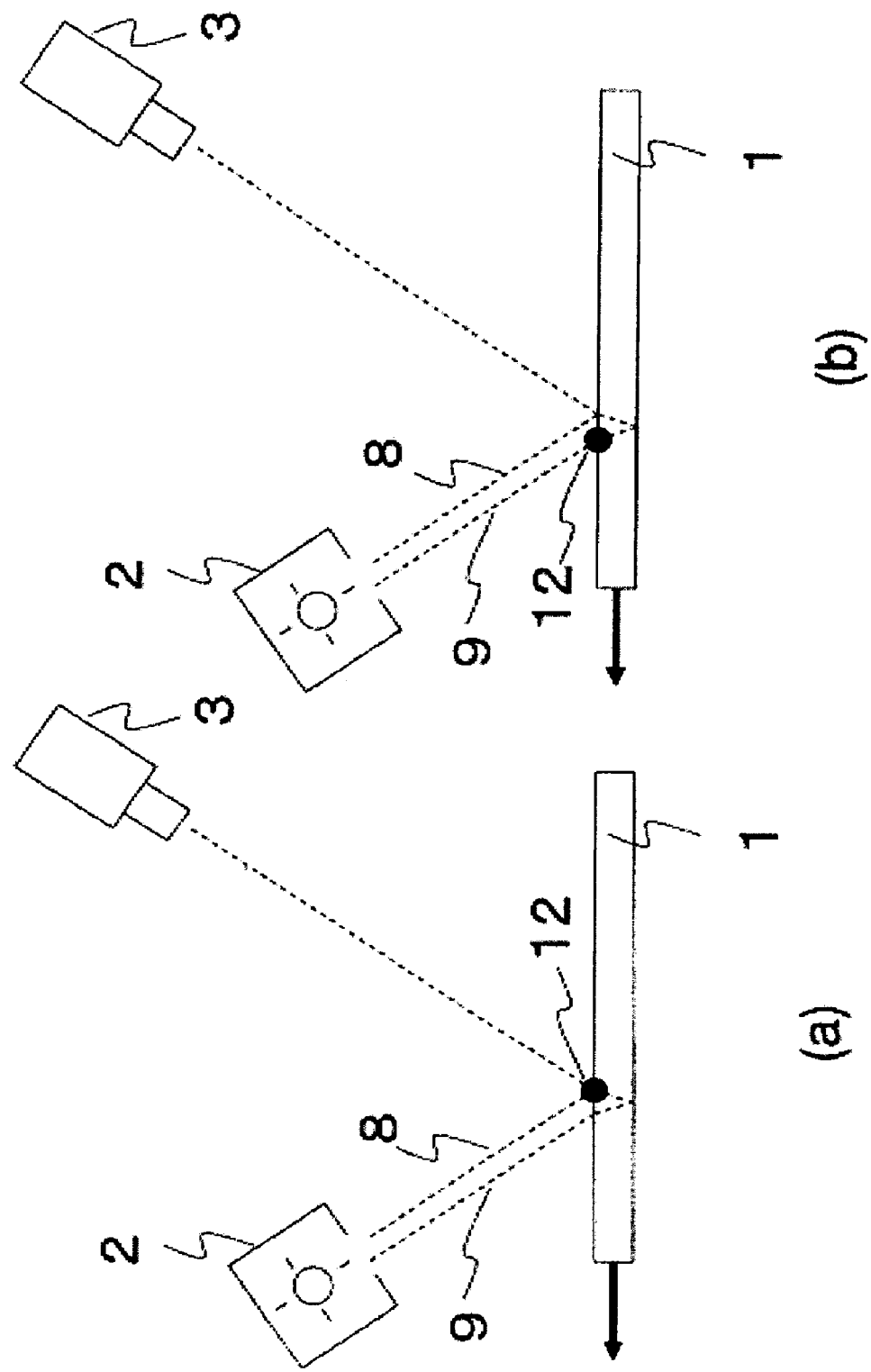
FIG. 3 includes views showing states in which the upper line sensor camera takes images of a defect located on a main surface of a transparent plate material.

A step of searching for a defect candidate will be described next. FIG. 2(a) shows a state in which the line sensor camera 3 obtains a bright field. In FIG. 2(a), light emitted from the linear light source 2 reaches the line sensor camera 3 mainly via two optical paths. One optical path 8 is formed by reflection at the main surface of the transparent plate material 1 (an upper surface of the transparent plate material 1); and the other optical path 9 is formed by reflection at the rear surface of the transparent plate material 1 (a lower surface of the transparent plate material 1). Images formed via the two optical paths 8 and 9 overlap at the line sensor camera 3 to form a bright field.

In the same way, FIG. 2(b) shows a state in which the line sensor camera 5 obtains a bright field. In FIG. 2(b), light emitted from the linear light source 4 reaches the line sensor camera 5 mainly via two optical paths. One optical path 10 is formed by reflection at the rear surface of the transparent plate material 1; and the other optical path 11 is formed by reflection at the main surface of the transparent plate material 1. Images formed via the two optical paths 10 and 11 overlap at the line sensor camera 5 to form a bright field.

Next, a step of determining, according to the contrast of an image of a defect candidate obtained by such search, whether the image is a real image or a virtual image will be described. When a defect crosses an optical path, light reaching the line sensor camera from its corresponding linear light source is weakened or, in some cases, strengthened due to optical behavior exhibited by the defect (such as refraction, scattering, reflection, absorption, or light-blocking). As a result, the line sensor camera acquires the defect as a darker image, or in some cases a brighter image, than the surrounding bright field. Patterns of generating images of defects and pseudo defects will be described below by referring to FIG. 3 to FIG. 12.

Figure 4:
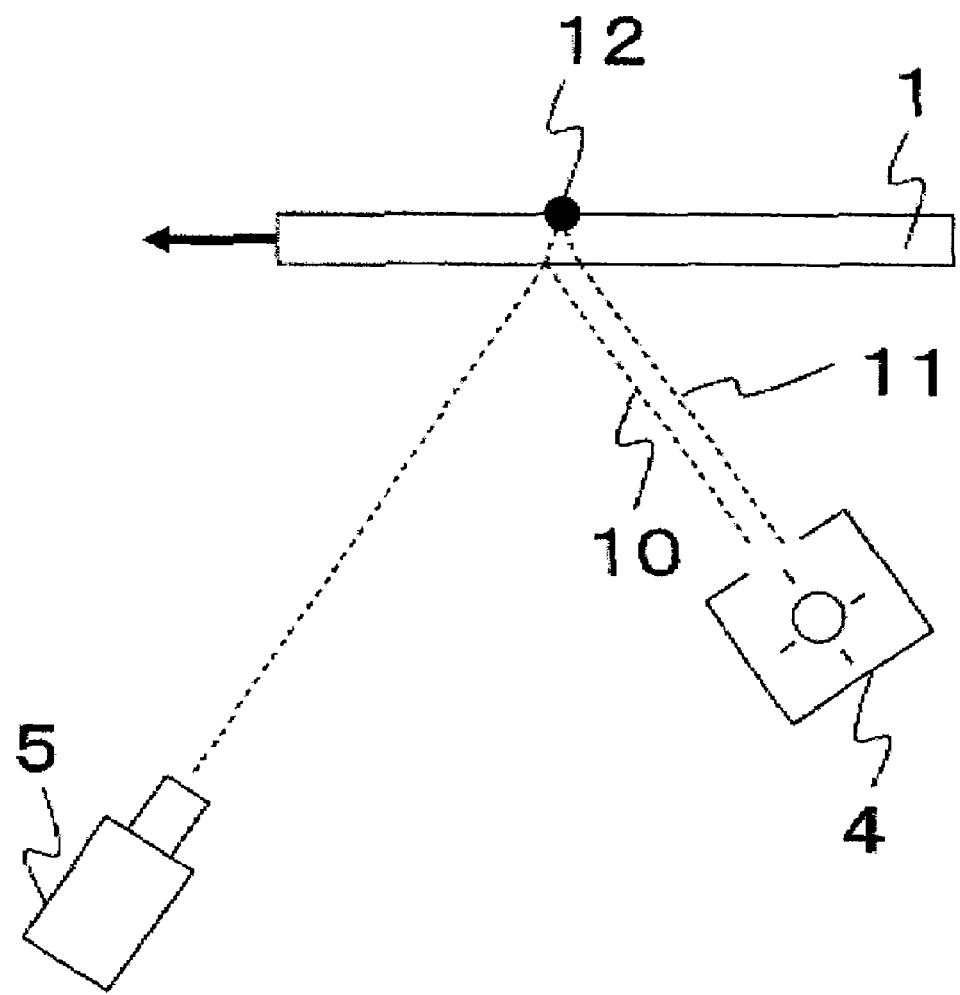
FIG. 4 is a view showing a state in which the lower line sensor camera takes an image of the defect located on the main surface of the transparent plate material.
Figure 5:
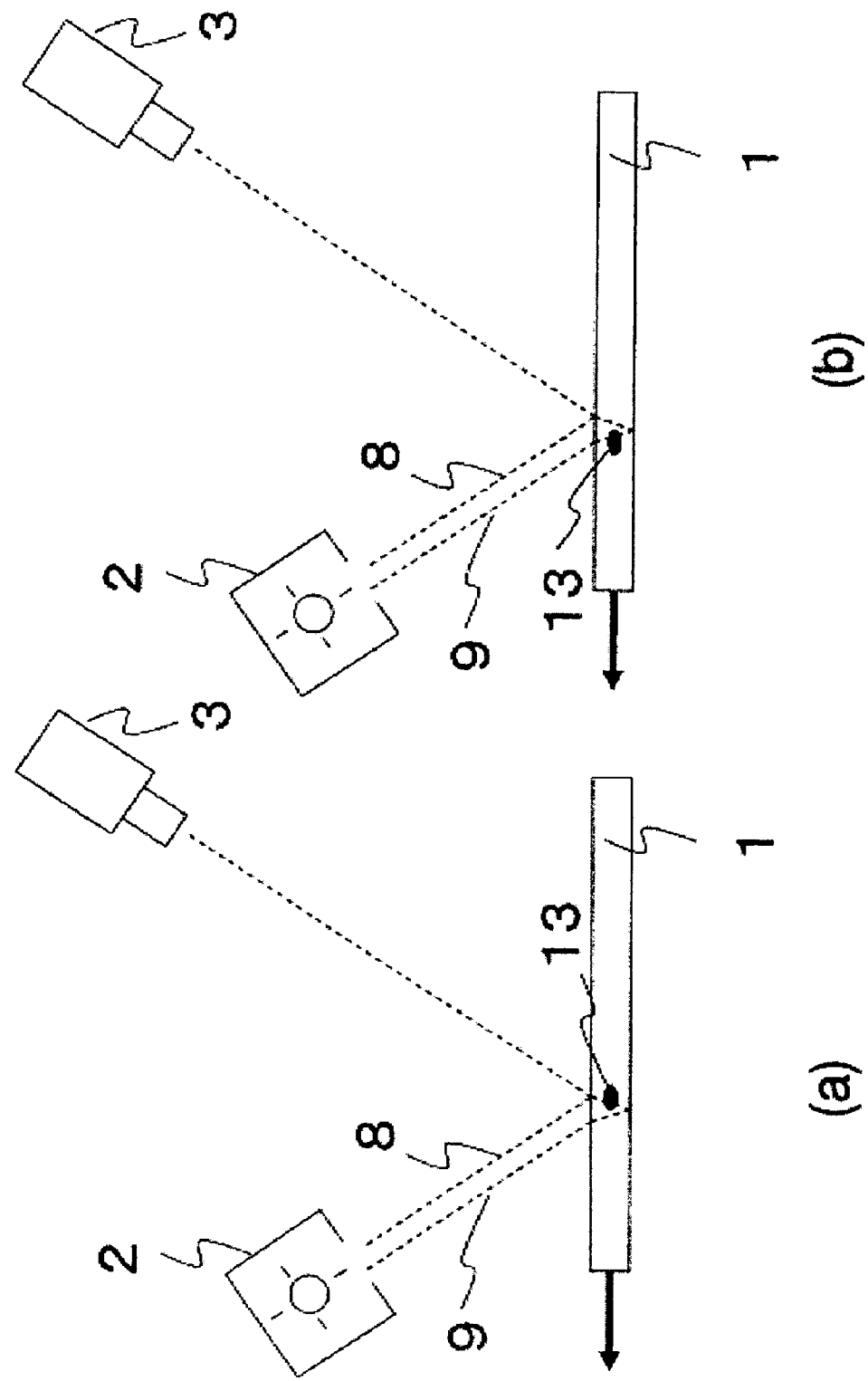
FIG. 5 includes views showing states in which the upper line sensor camera takes images of a defect located inside the transparent plate material.
Figure 6:
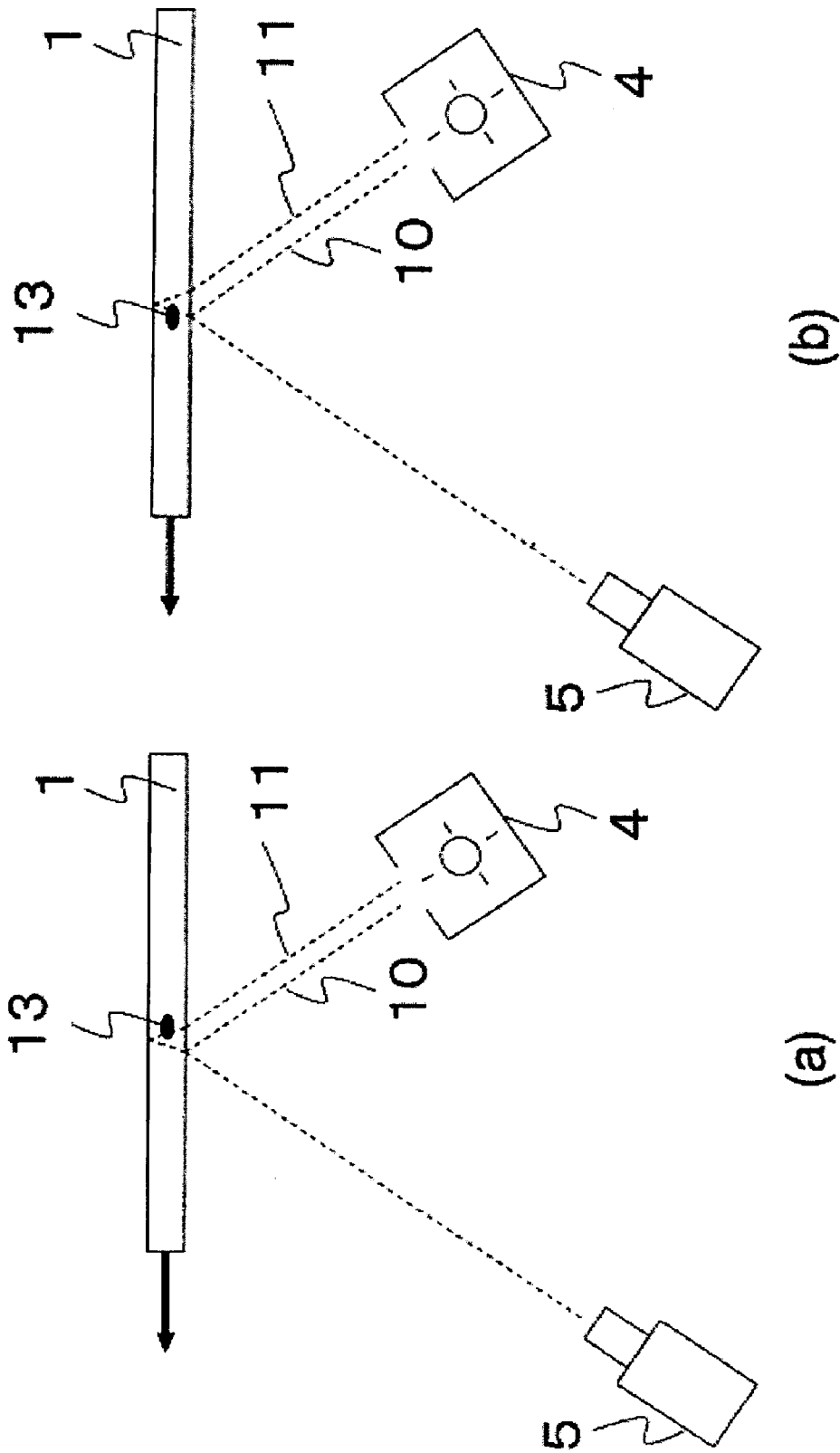
FIG. 6 includes views showing states in which the lower line sensor camera takes images of the defect located inside the transparent plate material.

FIG. 3(a), FIG. 3(b), and FIG. 4 show states in which the line sensor cameras 3 and 5 take images of a defect 12 located on the main surface of the transparent plate material 1. In particular, FIG. 3(a) shows a state in which the defect 12 crosses the optical path 8 and the optical path 9 at the same time. The defect 12 causes optical behavior to occur in the light advancing via each of the optical path 8 and the optical path 9. As a result, the line sensor camera 3 takes a real image of the defect 12 with images formed via the two optical paths 8 and 9 superimposed.

FIG. 3(b) shows a state in which the defect 12 crosses only the optical path 9 when the transparent plate material 1 is further conveyed. The defect 12 causes optical behavior to occur only in the light advancing via the optical path 9. As a result, the line sensor camera 3 takes a virtual image of the defect 12 with images via the two optical paths 8 and 9 superimposed. FIG. 4 shows a state in which the defect 12 crosses only the optical path 11. The defect 12 causes optical behavior to occur only in the light advancing via the optical path 11. As a result, the line sensor camera 5 takes a virtual image of the defect 12 with images via the two optical paths 10 and 11 superimposed.

FIG. 5(a), FIG. 5(b), FIG. 6(a), and FIG. 6(b) show states in which the line sensor cameras 3 and 5 take images of a defect 13 located inside the transparent plate material 1. FIG. 5(a) shows a state in which the defect 13 crosses only the optical path 9. The defect 13 causes optical behavior to occur only in the light advancing via the optical path 9. As a result, the line sensor camera 3 takes a virtual image of the defect 13 with images via the two optical paths 8 and 9 superimposed. FIG. 5(b) shows a state in which the defect 13 crosses only the optical path 9 when the transparent plate material 1 is further conveyed. The defect 13 causes optical behavior to occur only in the light advancing via the optical path 9. As a result, the line sensor camera 3 takes a virtual image of the defect 13 with images via the two optical paths 8 and 9 superimposed. FIG. 6(a) shows a state in which the defect 13 crosses only the optical path 11. The defect 13 causes optical behavior to occur only in the light advancing via the optical path 11. As a result, the line sensor camera 5 takes a virtual image of the defect 13 with images via the two optical paths 10 and 11 superimposed. FIG. 6(b) shows a state in which the defect 13 crosses only the optical path 11 when the transparent plate material 1 is further conveyed. The defect 13 causes optical behavior to occur only in the light advancing via the optical path 11. As a result, the line sensor camera 5 takes a virtual image of the defect 13 with images via the two optical paths 10 and 11 superimposed.

Figure 7:
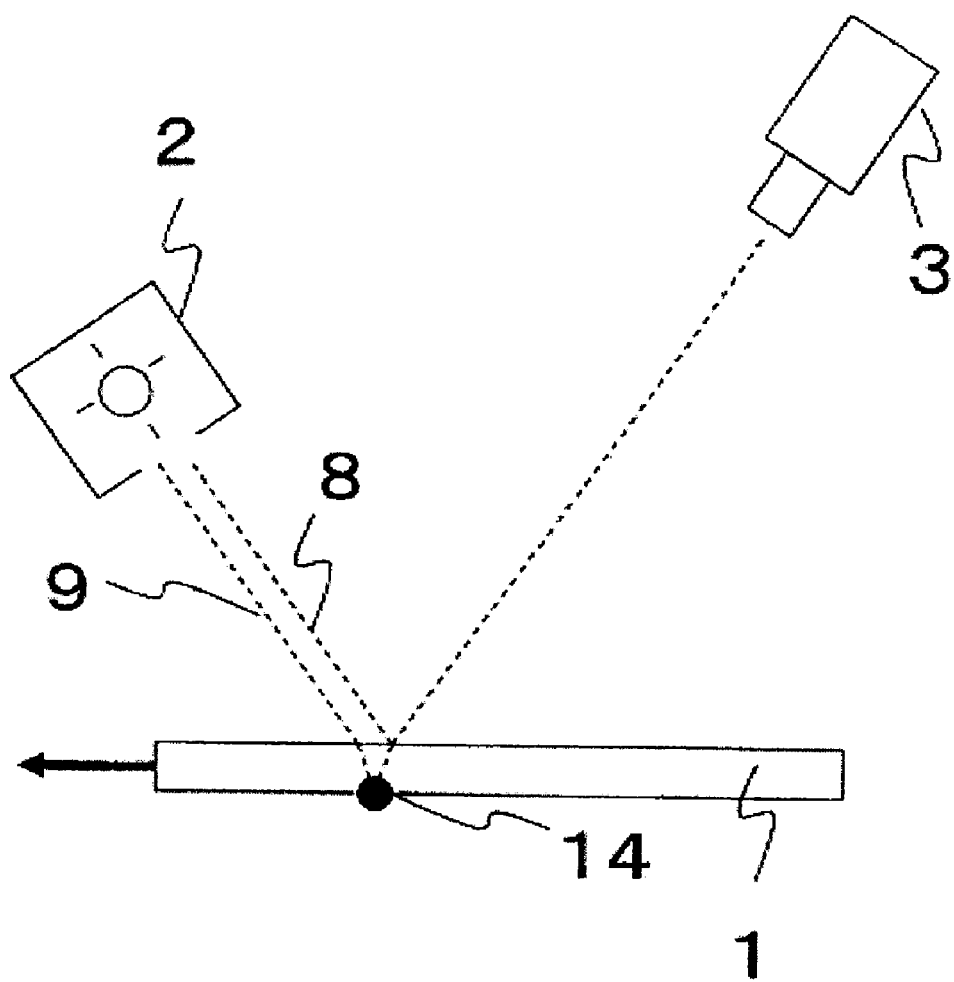
FIG. 7 is a view showing a state in which the upper line sensor camera takes an image of a defect located on a rear surface of the transparent plate material.
Figure 8:
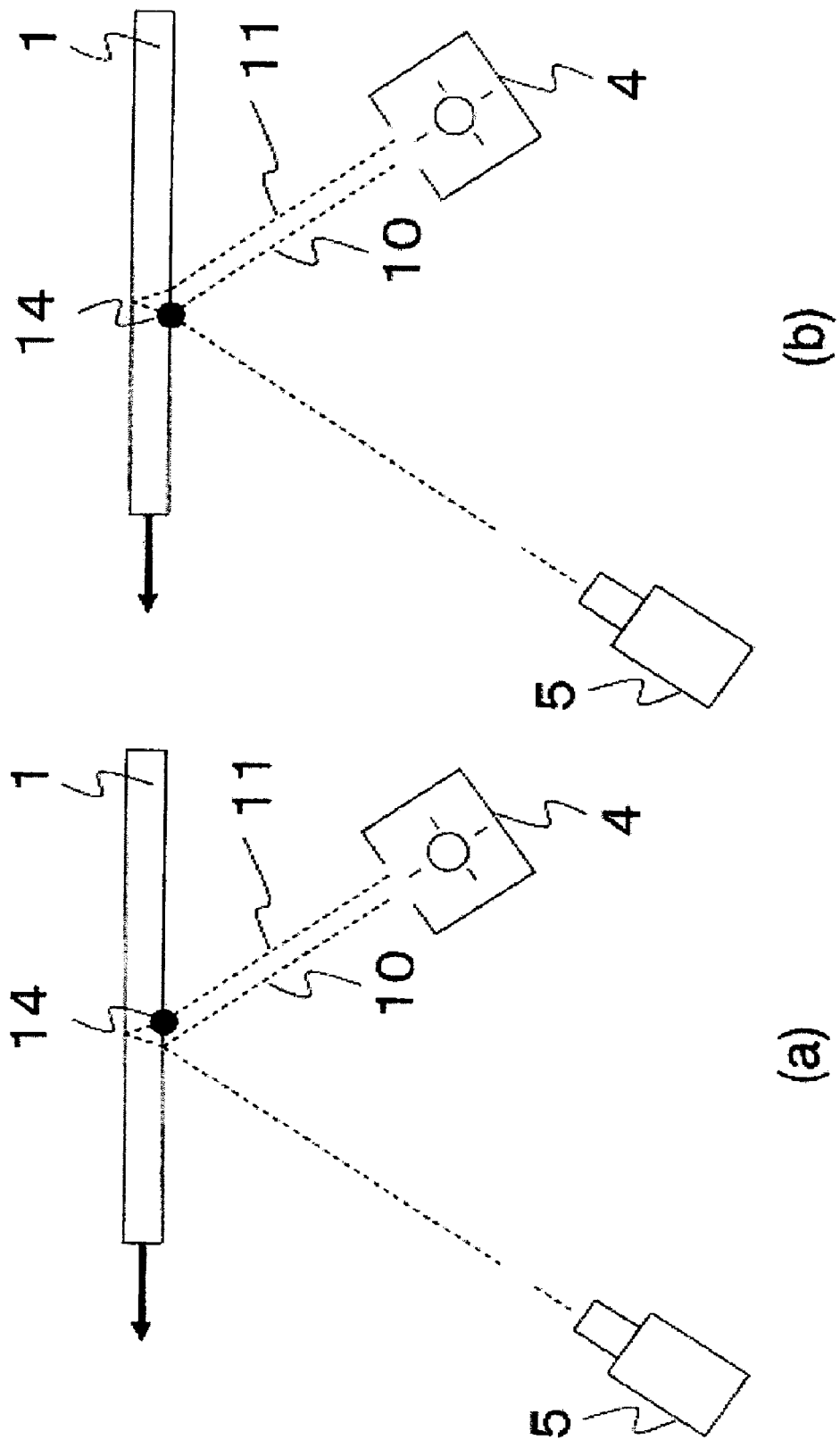
FIG. 8 includes views showing states in which the lower line sensor camera takes images of the defect located on the rear surface of the transparent plate material.
Figure 9:
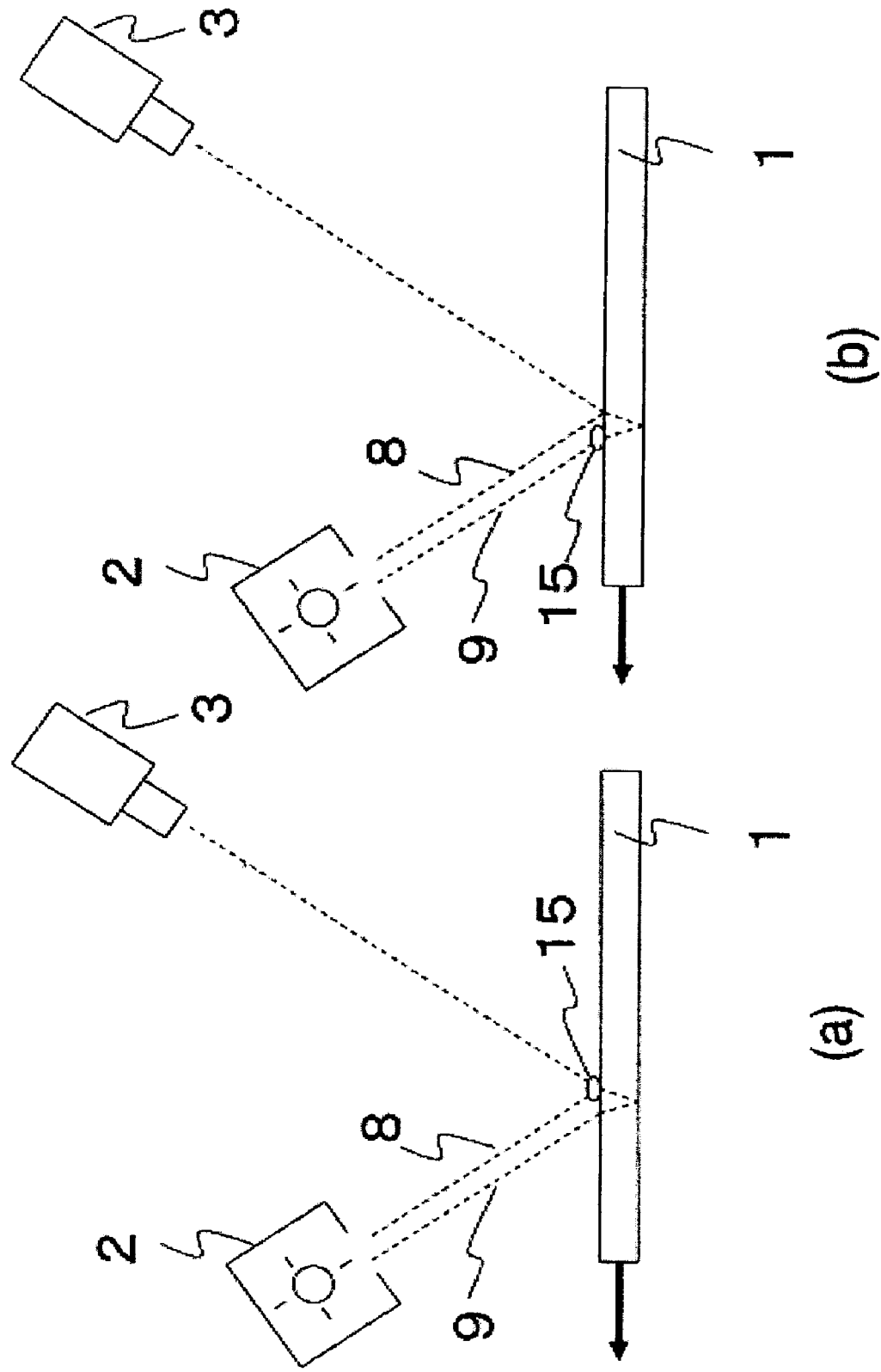
FIG. 9 includes views showing states in which the upper line sensor camera takes images of a pseudo defect located on the main surface of the transparent plate material.

FIG. 7, FIG. 8(a), and FIG. 8(b) show states in which the line sensor cameras 3 and 5 take images of a defect 14 located on the rear surface of the transparent plate material 1. In particular, FIG. 7 shows a state in which the defect 14 crosses only in the optical path 9. The defect 14 causes optical behavior to occur only the light advancing via the optical path 9. As a result, the line sensor camera 3 takes a virtual image of the defect 14 with images via the two optical paths 8 and 9 superimposed. FIG. 8(a) shows a state in which the defect 14 crosses only the optical path 11. The defect 14 causes optical behavior to occur only in the light advancing via the optical path 11. As a result, the line sensor camera 3 takes a virtual image of the defect 14 with images via the two optical paths 10 and 11 superimposed.

FIG. 8(b) shows a state in which the defect 14 crosses the optical path 10 and the optical path 11 at the same time when the transparent plate material 1 is further conveyed. The defect 14 causes optical behavior to occur in the light advancing via each of the optical path 10 and the optical path 11. As a result, the line sensor camera 5 takes a real image of the defect 14 with images via the two optical paths 10 and 11 superimposed.

Figure 10:
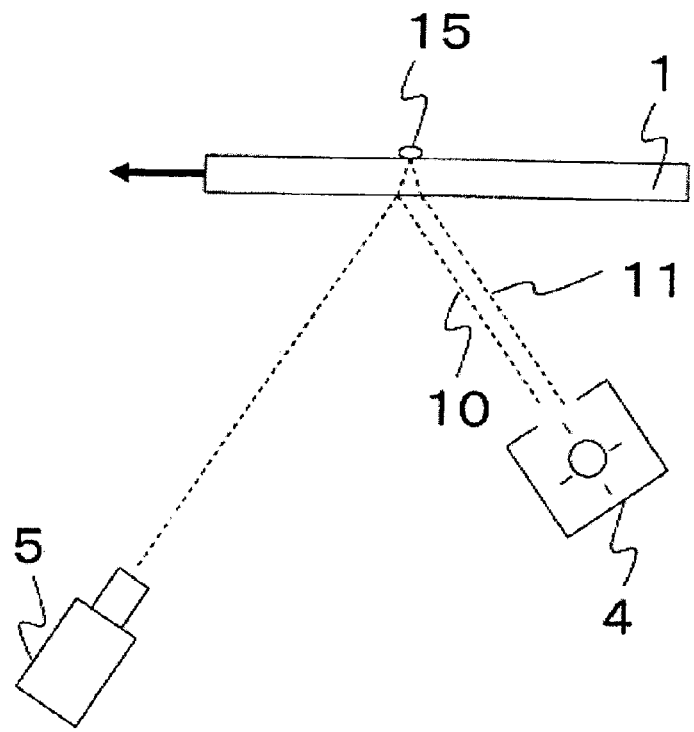
FIG. 10 is a view showing a state in which the lower line sensor camera takes an image of the pseudo defect located on the main surface of the transparent plate material.

FIG. 9(a), FIG. 9(b), and FIG. 10 show states in which the line sensor cameras 3 and 5 take images of a pseudo defect 15 located on the main surface of the transparent plate material 1. In particular, FIG. 9(a) shows a state in which the pseudo defect 15 crosses the optical path 8 and the optical path 9 at the same time. The pseudo defect 15 causes optical behavior to occur in the light advancing via each of the optical path 8 and the optical path 9. As a result, the line sensor camera 3 takes a real image of the pseudo defect 15 with images via the two optical paths 8 and 9 superimposed. FIG. 9(b) shows a state in which the pseudo defect 15 crosses only in the optical path 9 when the transparent plate material 1 is further conveyed. The pseudo defect 15 causes optical behavior to occur only in the light advancing via the optical path 9. As a result, the line sensor camera 3 takes a virtual image of the pseudo defect 15 with images via the two optical paths 8 and 9 superimposed.

FIG. 10 shows a state in which the pseudo defect 15 is located at a reflection point of the optical path 11. Since the pseudo defect 15 is located outside the transparent plate material 1, the pseudo defect 15 does not causes optical behavior to occur in the light advancing via the optical path 11. As a result, the line sensor camera 5 obtains no image of the pseudo defect 15.

Figure 11:
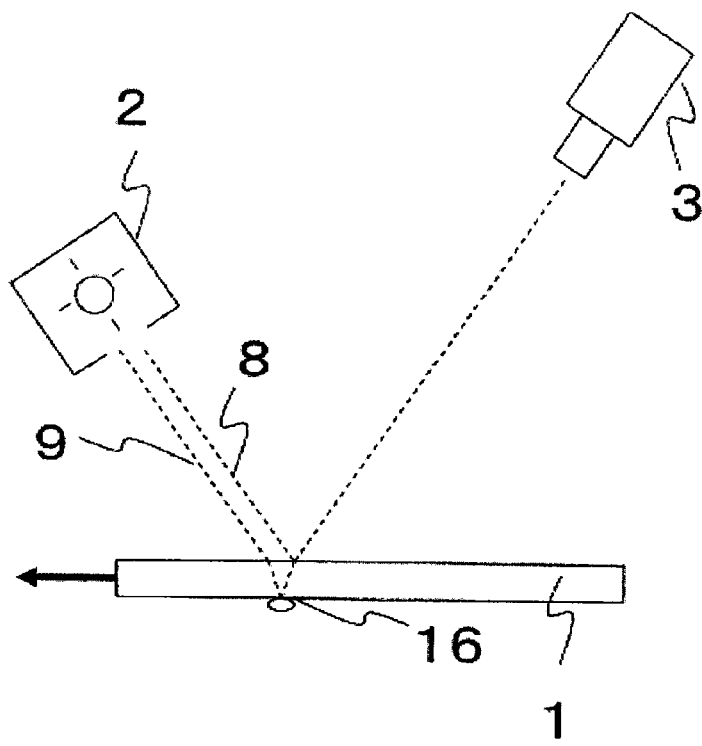
FIG. 11 is a view showing a state in which the upper line sensor camera takes an image of a pseudo defect located on the rear surface of the transparent plate material.
Figure 12:
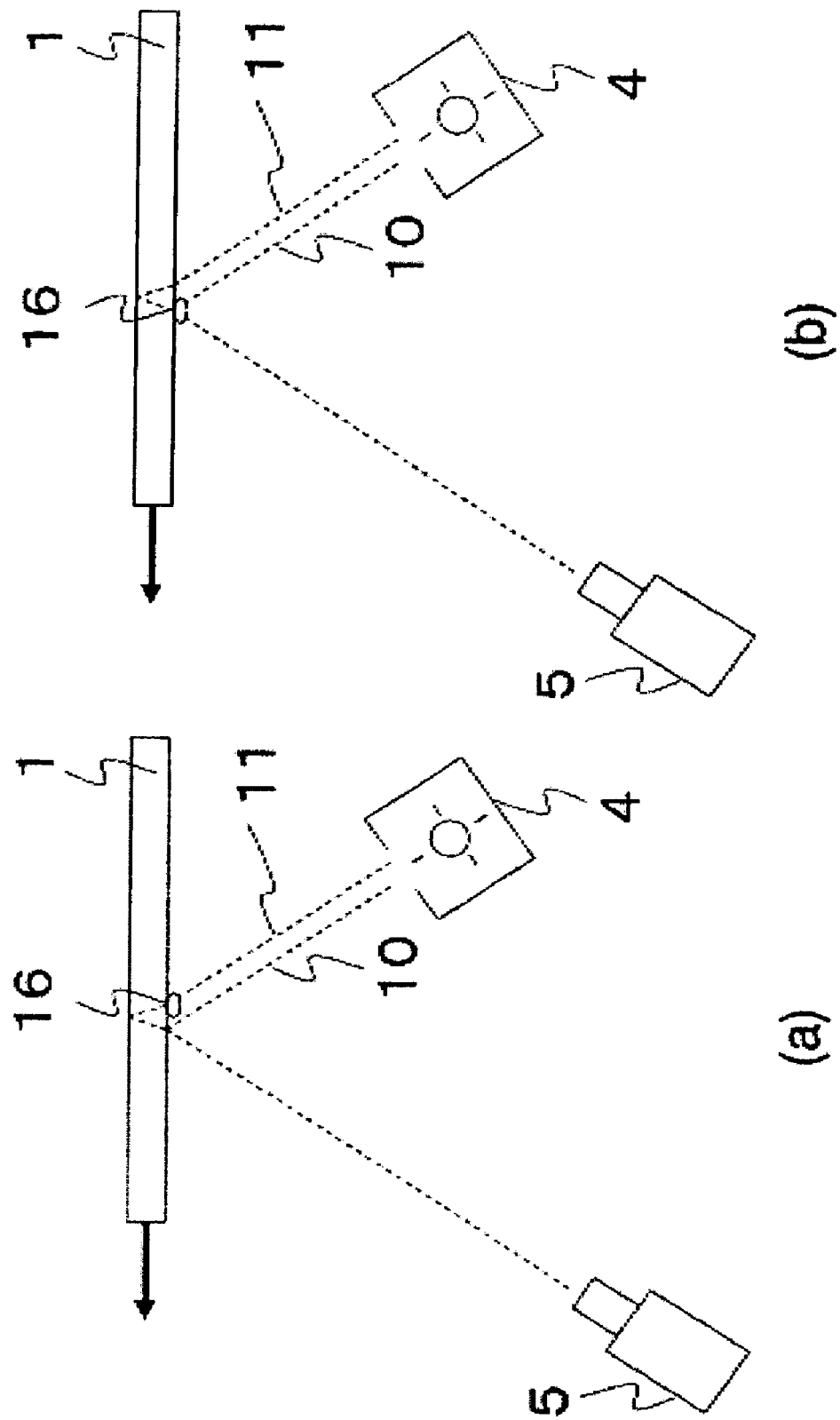
FIG. 12 includes views showing states in which the lower line sensor camera takes images of the pseudo defect located on the rear surface of the transparent plate material.
Figure 13:
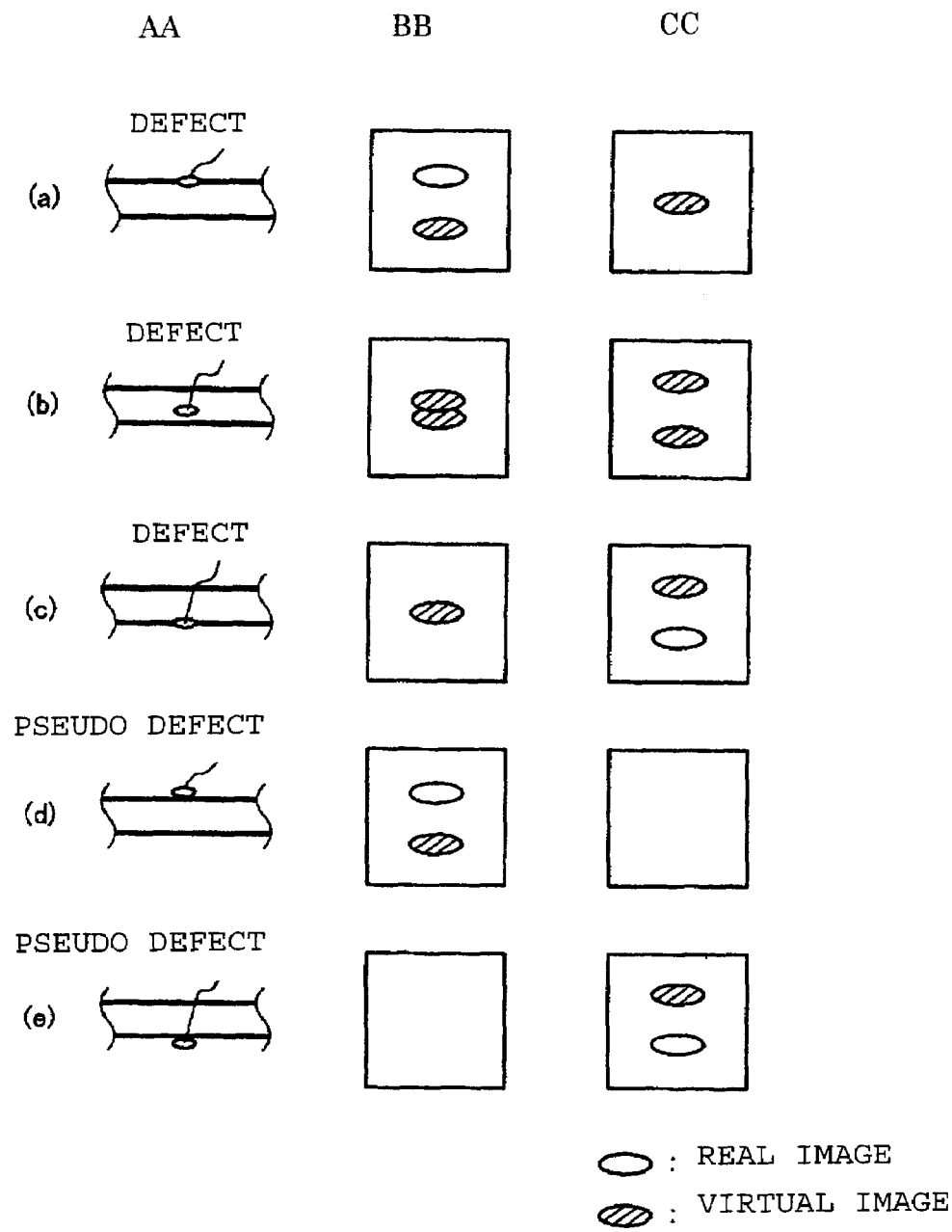
FIG. 13 includes views showing the relationships between the types of defects etc., and images captured by the cameras.

FIG. 11, FIG. 12(a), and FIG. 12(b) show states in which the line sensor cameras 3 and 5 take images of a pseudo defect 16 located on the rear surface of the transparent plate material 1. In particular, FIG. 11 shows a state in which the pseudo defect 16 is located at a reflection point of the optical path 9. Since the pseudo defect 16 is located outside the transparent plate material 1, the pseudo defect 16 does not causes optical behavior to occur in the light advancing via the optical path 9. As a result, the line sensor camera 3 obtains no image of the pseudo defect 16.

FIG. 12(a) shows a state in which the pseudo defect 16 crosses only the optical path 11. The pseudo defect 16 causes optical behavior to occur only in the light advancing via the optical path 11. As a result, the line sensor camera 3 takes a virtual image of the pseudo defect 16 with images via the two optical paths 10 and 11 superimposed. FIG. 12(b) shows a state in which the pseudo defect 16 crosses the optical path 10 and the optical path 11 at the same time when the transparent plate material 1 is further conveyed. The pseudo defect 16 causes optical behavior to occur in the light advancing via each of the optical path 10 and the optical path 11. As a result, the line sensor camera 5 takes a real image of the pseudo defect 16 with images via the two optical paths 10 and 11 superimposed.

Next, a step of regarding a defect candidate as a pseudo defect will be described. Since pseudo defects, such as dust and grime, are not located inside a transparent plate material but are attached to the main surface or the rear surface (something located inside is treated as a defect), the descriptions made by referring to FIG. 9 to FIG. 12 cover the appearance patterns of images of defects and pseudo defects.

The step of regarding a defect candidate as a pseudo defect and a step of identifying which of the main surface, the inside and the rear surface of the transparent plate material has the defect candidate, will be described. FIG. 13(a) to FIG. 13(e) show the relationships between the types of defects etc., and images captured by the cameras. As shown in FIG. 13(a) to FIG. 13(e), image patterns of defect candidates, which are captured by the line sensor cameras differ, depending on the types and locations of defects etc. Table 1 lists appearance patterns of images taken by the line sensor cameras for defects and pseudo defects. When a line sensor camera takes two images of a defect, these images are handled as a pair, hereinafter called a "dual images".

TABLE 1

| | Location of defects etc. | Line sensor camera at main surface side | Line sensor camera at rear surface side |
|---|---|---|---|
| (1) | Defect on main surface | Real image and virtual image | Virtual image |
| (2) | Defect inside | Virtual images (two) | Virtual images (two) |
| (3) | Defect on rear surface | Virtual image | Real image and virtual image |
| (4) | Pseudo defect on main surface | Real image and virtual image | No image |
| (5) | Pseudo defect on rear surface | No image | Real image and virtual image |

When a defect is inside the transparent plate material, this table indicates that the upper and lower line sensor cameras take two virtual images. However, if the defect is close to the main surface or the rear surface, the two virtual images are superimposed to apparently be only one image in some cases. For example, if this inside defect is located close to the rear surface, the virtual images captured by the upper line sensor camera are superimposed to apparently be only one image in some cases. In the same way, if this inside defect is located close to the main surface, the virtual images captured by the lower line sensor camera are superimposed to apparently be only one image in some cases.

Even in such a case, since the two line sensor cameras are used in the present invention, the position of a defect in the thickness direction of the transparent plate material can be correctly identified based on the images captured by one of the two line sensor cameras that does not take virtual images in a superimposed manner. In that case, the present invention uses the contrasts of dual images or the distance between two images forming the dual images.

First, a method using the contrasts of dual images will be described. When both a real image and a virtual image of a defect or a pseudo defect are taken, the real image has a higher contrast. This is because two optical paths cross that defect in the formation of the real image, whereas only one optical path crosses that defect in the formation of the virtual image. As understood from Table 1, dual images captured by a line sensor camera comprise a combination of a real image and a virtual image when the defect is on the main surface or the rear surface. On the other hand, when a defect is located inside the transparent plate material, dual images comprise a combination of virtual images. In general, when a defect is located on the main surface or the rear surface of a transparent plate material, there is a contrast difference between the dual images; and when a defect is located inside the transparent plate material, there is no contrast difference between the dual images. Therefore, by comparing the contrasts of a dual images, it can be determined whether the defect is located inside the transparent plate material or on the main surface (or the rear surface) thereof.

Next, a method using the distance between the two images forming a dual images will be described.

Figure 14:
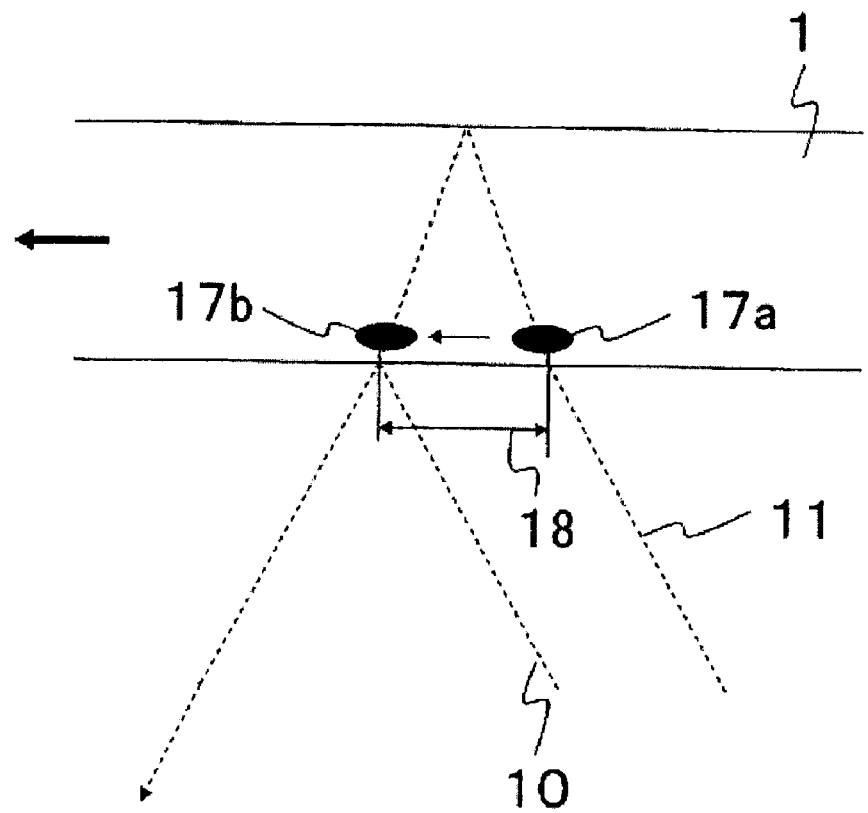
FIG. 14 is a view showing a state in which the lower line sensor camera takes images of an inside defect located close to the rear surface of the transparent plate material.

FIG. 14 shows a state in which the line sensor camera 5 takes images of an inside defect 17 located close to the rear surface. There are two instances where the line sensor camera 5 takes an image of the defect 17. One instance is when the inside defect 17 is located at a point 17a, and the other instance is when the inside defect is located at a point 17b. The distance 18 between the points 17a and 17b is proportional to the depth of the defect 17 from the main surface of the transparent plate material 1.

A step of determining the distance between two images for a defect candidate, captured by a camera, will be described. When the transparent plate material 1 is conveyed at a constant speed and the line sensor camera scans at a constant speed, the distance 18 is observed as the distance between the two images forming a dual images. Next, a step of identifying, based on the distance between the two images, which of the main surface, the inside, and the rear surface of the transparent plate material has the defect candidate will be described. The distance 18 becomes longest when the defect is on the rear surface. When the maximum value of the distance between the two images forming dual images is known in advance, it can be determined whether the defect 17 is inside the transparent plate material or on the rear surface thereof, by comparing the actual distance between the two images forming the dual images with the maximum value.

The explanation of FIG. 14 has been made about a case where the inside defect is located close to the rear surface. An inside defect located close to the main surface can also be distinguished in the same way. In that case, it can be determined whether the defect is inside the transparent plate material 1 or on the main surface thereof, by using the dual images captured by the line sensor camera 3, which is positioned above the transparent plate material 1.

A step of obtaining the depth of a defect in the thickness direction of the transparent plate material will be further described. As described above, according to the present invention, when not only the position where a defect is located with respect to the transparent plate material (on the main surface, in the inside, or on the rear surface) is known but also the thickness of the transparent plate material is known, the distance between the two images forming the dual images can be converted to the depth of the defect by using the fact that the distance 18 is proportional to the depth of the defect.

EXAMPLES

Next, examples of the present invention will be described. It should be clearly understood that these examples do not limit the present invention.

The utility of the present invention was tested by using a glass substrate having a thickness of 0.7 mm for an LCD panel (hereinafter called the glass substrate) as a transparent plate material, which will be described below in detail. According to the basic structure shown in FIG. 1, reflective bright-field optical systems were prepared, using two line sensor cameras and two linear light sources that employed fluorescent lights, and the systems were arranged above and below the glass substrate. The angle formed between the optical axis of each line sensor camera and the normal line of the glass substrate was set to 30 degrees. Conveying rollers 6 conveyed the glass substrate at a conveying speed of 100 mm/s.

The line sensor cameras continuously performed scanning and took images in the vicinities of defects and pseudo defects. Images for a defect or a pseudo defect (in other words, images of a defect candidate) captured by the upper and lower line sensor cameras were combined, and attempts were made to distinguish between a defect and a pseudo defect, to identify the position of a defect in the thickness direction of the glass substrate, and to measure the depth of the defect in the thickness direction of the glass substrate.

Figure 15:
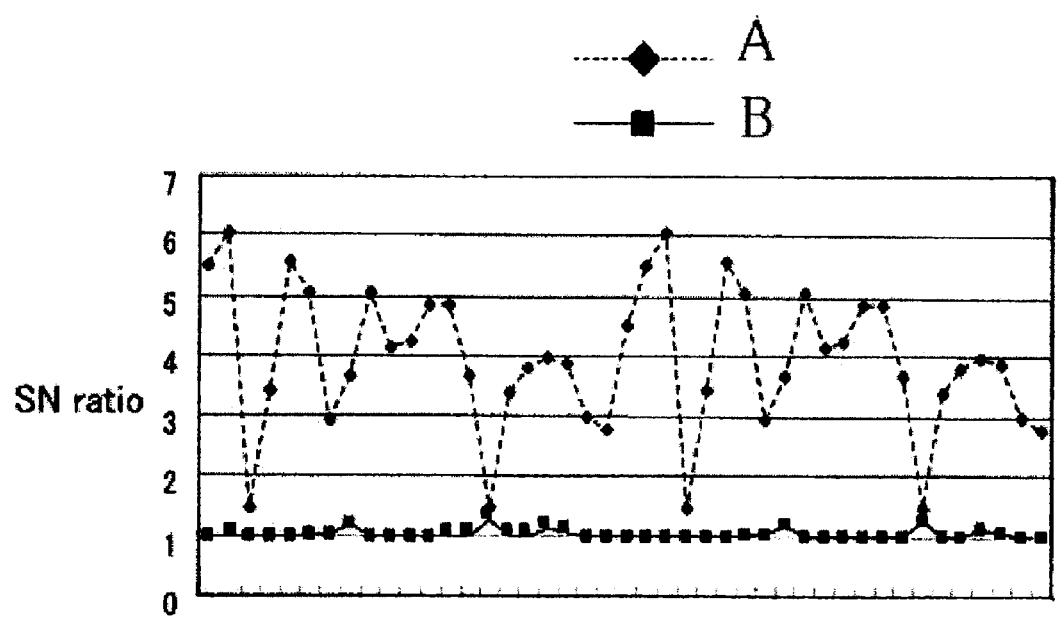
FIG. 15 is a view showing results of attempts to distinguish between defects and pseudo defects according to the present invention (example)

FIG. 15 shows examination results of detection signals output from the upper and lower line sensor cameras, which were obtained when dust particles as pseudo defects were scattered in advance on a main surface of the glass substrate. In FIG. 15, line A indicates the detection signals of the line sensor camera positioned above the glass substrate; line B indicates the detection signals of the line sensor camera positioned below the glass substrate; the horizontal axis indicates individual pseudo defects; and the vertical axis indicates the magnitudes of the detection signals of the upper and lower line sensor cameras. The magnitudes of the detection signals are represented by the S/N ratios obtained by dividing the detection signals by noise levels. It is clear from FIG. 15 that the line sensor camera positioned above the glass substrate detected individual dust particles remarkably well, whereas the line sensor camera positioned below the glass substrate did not detect the dust particles. Therefore, from this test, it was confirmed that defects and pseudo defects could be distinguished.

Figure 16:
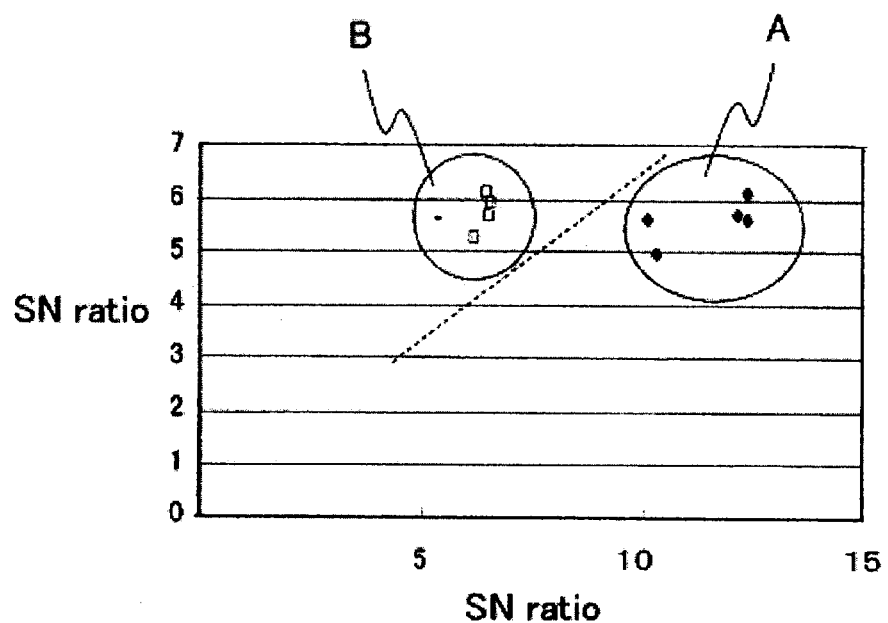
FIG. 16 is a view showing results of attempts to distinguish between defects located on the main surface and inside defects located close to the main surface according to the present invention (example)

FIG. 16 shows results of the attempts to distinguish between the positions of inside defects located within 10 μm (which had been measured in advance) from the main surface and the positions of defects on the main surface. In FIG. 16, group A indicates defects on the main surface; group B indicates defects located within 10 μm from the main surface; the horizontal axis indicates the magnitude of the detection signal of an image first appearing in the field of view of a line sensor camera, of the dual images of a defect; and the vertical axis indicates the magnitude of the detection signal of the image appearing for the second time in the field of view of the line sensor camera, of the dual images of the defect. In the same way as in FIG. 15, the magnitudes of the detection signals are represented by the S/N ratios. It is clear from FIG. 16 that defects located on the main surface and inside defects show differences in the magnitudes of the detection signals of the dual images (contrast). When a defect is on the main surface, the magnitude of the detection signal of an image first appearing in the field of view of the line sensor camera, of the dual images, is larger than the magnitude of the detection signal of the image appearing for the second time in the field of view of the line sensor camera.

On the other hand, when a defect is inside, even if it is located within 10 μm from the main surface, the magnitudes of the detection signals of the two images are close. Therefore, with this test, it was confirmed that the position of a defect could be identified in the thickness direction of the transparent plate material. The dotted line in the figure is, ideally, a straight line passing through the origin of the coordinate axes.

Figure 17:
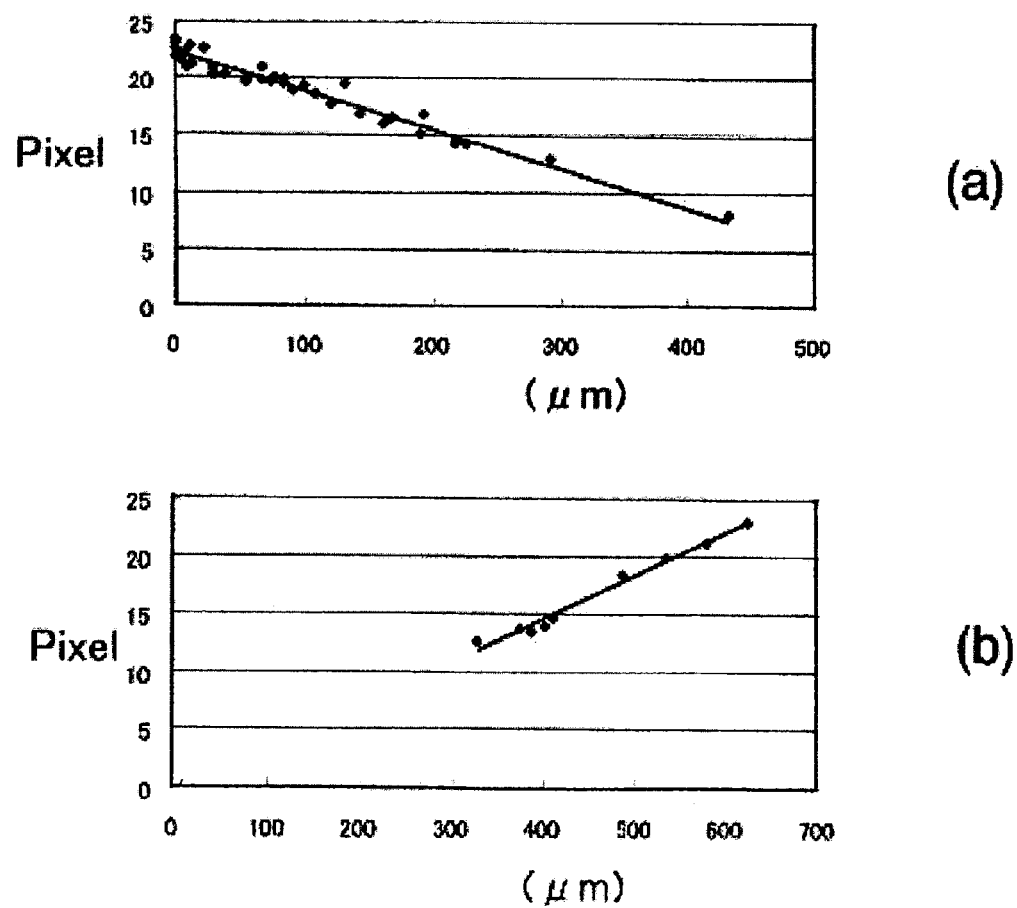
FIG. 17 includes views showing measurement results of the depths of defects according to the present invention (example).

FIG. 17 shows results of the depths of defects from the main surface, which were obtained from the distances between the two images forming dual images. FIG. 17(a) shows results obtained by the line sensor camera above the glass substrate; and FIG. 17(b) shows results obtained by the line sensor camera below the glass substrate. In each figure, the horizontal axis indicates the true values of the depths of the defects, separately measured, and the vertical axis indicates the distances between the two images forming dual images captured by the line sensor camera. It is clearly understood from these figures that the depths of the defects are proportional to the distances between the two images forming the dual images, wherein the depths and the distances have a proportional relationship described by a linear expression and have a high correlation therebetween. By using this relationship, the depth of a defect can be precisely obtained based on the distance between the two images forming the dual images. In the present invention, since cameras are disposed above and below a transparent plate material, even if the two images forming dual images are superimposed in one line sensor camera, the two images forming dual images are separated in the other line sensor camera. Thus, depending on the depths of defects, suitable line sensor cameras can be selected. Therefore, as shown in FIG. 17(a) and FIG. 17(b), the depths of defects can be measured over the entire thickness. With this test, it was confirmed that the depths of defects could be precisely measured.

INDUSTRIAL APPLICABILITY

As described above, according to the present invention, defects and pseudo defects can be distinguished, and the positions of defects can be identified with a higher precision in the thickness direction of a transparent plate material, and therefore, it is expected that the determination precision in defect inspection can be improved. In addition, since a transparent plate material is not required to have a smooth end face in the present invention, the present invention can be applied to continuous forming processes, such as the float process for flat glass, and defect information can be obtained quickly at an upstream stage in a process. Therefore, the present invention will greatly contribute to the construction of defect inspection systems that are superior to conventional systems.

The entire disclosure of Japanese Patent Application No. 2004-339215 filed on Nov. 24, 2004 including specification, claims, drawings and summary is incorporated herein by reference in its entirety.

The invention claimed is:

1. A defect inspection method for a transparent plate material for detecting a bubble, a scratch, a foreign matter, and another defect existing on or in the transparent plate material, the method comprising the steps of:

capturing a first image of a main surface of the transparent plate material by using a first reflective bright-field optical system disposed at a main surface side of the transparent plate material, the first optical system comprising a first linear light source and a first camera;

capturing a second image of a rear surface of the transparent plate material by using a second reflective bright-field optical system disposed at a rear surface side of the transparent plate material, the second optical system comprising a second linear light source and a second camera;

searching for a defect candidate in each of the first and second images;

checking, based on a result of the search, whether the defect candidate is located at positions corresponding to each other in the first and second images;

regarding the defect candidate as a defect, when the defect candidate is located in both the first and second images; and regarding the defect candidate as a pseudo defect, when the defect candidate is located in only one of the first and second images.

2. A defect inspection apparatus for a transparent plate material for detecting a bubble, a scratch, a foreign matter, and another defect existing on or in the transparent plate material, the apparatus comprising:

a first reflective bright-field optical system disposed at a main surface side of the transparent plate material, configured to capture a first image of a main surface of the transparent plate material, the first optical system comprising a first linear light source and a first camera;

a second reflective bright-field optical system disposed at a rear surface side of the transparent plate material, configured to capture a second image of a rear surface of the transparent plate material, the second optical system comprising a second linear light source and a second camera; and a computer configured to search for a defect candidate in each of the first and second images, to check, based on a result of the search, whether the defect candidate is located at positions corresponding to each other in the first and second images, to regard the defect candidate as a defect, when the defect candidate is located in both the first and second images, and to regard the defect candidate as a pseudo defect, when the defect candidate is located in only one of the first and second images.

* * * * *